United States Patent

Graiver et al.

[11] Patent Number: 5,856,546
[45] Date of Patent: Jan. 5, 1999

[54] METHOD FOR THE PREPARATION OF POTASSIUM SILANOLATES

[75] Inventors: Daniel Graiver, Midland; Arnold Wade Lomas, Rhodes; Edward Thomas Rasmussen, Jr.; Kelly James Wall, both of Midland, all of Mich.

[73] Assignee: Dow Corning Corporation, Midland, Mich.

[21] Appl. No.: 989,676

[22] Filed: Dec. 12, 1997

[51] Int. Cl.$^6$ ............................................. C07F 7/08
[52] U.S. Cl. ........................ 556/459; 556/450; 556/451; 556/457
[58] Field of Search .................... 556/450, 451, 556/457, 459

[56] References Cited

U.S. PATENT DOCUMENTS

| | | | |
|---|---|---|---|
| 3,453,304 | 7/1969 | Selin | 556/459 |
| 3,481,965 | 12/1969 | Selin | 556/459 |
| 3,578,726 | 5/1971 | Bostick et al. | 260/825 |
| 3,641,090 | 2/1972 | Bostick et al. | 260/448.2 |
| 4,281,147 | 7/1981 | Koerner et al. | 556/459 |

*Primary Examiner*—Paul F. Shaver
*Attorney, Agent, or Firm*—Melvin D. Fletcher

[57] ABSTRACT

A method for the preparation of potassium silanolates comprising reacting a mixture comprising solid potassium hydroxide and a polyorganosiloxane described by formula $R^1 R^1R^2_2SiO(R^2_2SiO)_m R^3$ or $(R^2_2SiO)_n$, where m is an integer from 1 to about 1000, n is an integer from 3 to about 20, $R^1$ a hydroxyl group or an alkoxy group comprising from 1 to about 8 carbon atoms and $R^2$ is a hydrogen atom or an independently selected substituted or unsubstituted monovalent hydrocarbon group comprising from 1 to about 8 carbon atoms $R^3$ is a hydrogen atom or an alkyl group comprising from 1 to 8 carbon atoms in the presence of an organic solvent which forms an azeotrope with water at a temperature within a range of about 90° C. to 150° C. thereby forming a potassium silanolate.

17 Claims, No Drawings

METHOD FOR THE PREPARATION OF POTASSIUM SILANOLATES

BACKGROUND OF THE INVENTION

The invention is a method for the preparation of potassium silanolates. The method comprises reacting a mixture comprising solid potassium hydroxide and a polyorganosiloxane in the presence of an organic solvent which forms an azeotrope with water at a temperature within a range of about 90° C. to 150° C. thereby forming a potassium silanolate.

Bostick et al., U.S. Pat. No. 3,641,090, teach the preparation of hexamethylphosphoramide complexes made by effecting contact between hexamethylphosphoramide and an alkali metal silanolate. The hexamethylphosphoramide complex is useful as polymerization initiators for polyorganosiloxanes and polyorganosiloxane block copolymers. Bostick et al., does not teach making potassium silanolates using solid hydroxide.

In the process as taught by Bostick et al., large quantities of water must be removed in order to drive the reaction to completion and to minimize problems with phase separation, poor shelf-life, high branching, and quality variance. Water and residual solvent are typically removed from the reaction by distillation followed by high temperature stripping. However, under these conditions batch time is about 24 hours and the prolonged elevated temperatures during distillation and stripping can cause excessive cleavage of carbon-silicon bonds resulting in phase separation, poor shelf-life, quality variance, and high branching in the final product.

The present inventors have discovered that preparing potassium silanolates with solid potassium hydroxide eliminates the need to remove large quantities of water at elevated temperatures which is believed to cause the above problems. Another advantage is that the time to prepare potassium silanolates can be shortened from 24 hours to about 12 hours. Another advantage is water can be removed from the potassium silanolate by azeotropic distillation at lower temperatures than conventional distillation methods, thus reducing the degree of branching in the final product. Another advantage is that residual water and solvent can be stripped from the potassium silanolate at lower temperatures and in a shorter time period than for conventional stripping methods. Another advantage is that the potassium silanolates can be stored over an extended time period without the phase separation problems of known silanolate preparations.

SUMMARY OF INVENTION

The present invention is a method for the preparation of potassium silanolates. The method comprises reacting a mixture comprising solid potassium hydroxide and a polyorganosiloxane described by formula $R^1R^2_2SiO(R^2_2SiO)_mR^3$ or $(R^2_2SiO)_n$, where m is an integer from 1 to about 1000, n is an integer from 3 to about 20, $R^1$ is a hydroxyl group or an alkoxy group comprising from 1 to about 8 carbon atoms and $R^2$ is a hydrogen atom or an independently selected substituted or unsubstituted monovalent hydrocarbon group comprising from 1 to about 8 carbon atoms $R^3$ is a hydrogen atom or an alkyl group comprising from 1 to 8 carbon atoms in the presence of an organic solvent which forms an azeotrope with water at a temperature within a range of about 90° C. to 150° C. thereby forming a potassium silanolate.

DESCRIPTION OF INVENTION

The present invention is a method for the preparation of potassium silanolates. The method comprises reacting a mixture comprising solid potassium hydroxide and a polyorganosiloxane described by formula $R^1R^2_2SiO(R^2_2SiO)_mR^3$ or $(R^2_2SiO)_n$, where m is an integer from 1 to about 1000, n is an integer from 3 to about 20, $R^1$ is a hydroxyl group or an alkoxy group comprising from 1 to about 8 carbon atoms and $R^2$ is a hydrogen atom or an independently selected substituted or unsubstituted monovalent hydrocarbon group comprising from 1 to about 8 carbon atoms, $R^3$ is a hydrogen atom or an alkyl group comprising from 1 to 8 carbon atoms in the presence of an organic solvent which forms an azeotrope with water at a temperature within a range of about 90° C. to 150° C. thereby forming a potassium silanolate.

Reacting the mixture comprising solid potassium hydroxide and a polyorganosiloxane in the presence of an organic solvent which forms an azeotrope with water may be effected in standard reactors suitable for running equilibration type reactions.

The potassium hydroxide found to be useful in the present invention is in solid form rather than in aqueous solution. The solid potassium hydroxide can be in the form of pellets, flakes, or shavings, which are all commercially available. Using solid potassium hydroxide in the present method eliminates the need to remove large quantities of water in order to obtain stable potassium silanolate. Preferably, the solid potassium hydroxide should be completely dry, but commonly may contain up to 15 weight percent water. Solid potassium hydroxide containing more than 15 weight percent water may be used, but is undesirable because as more water is added to the reaction, longer distillation periods at higher temperatures are required to remove the additional water.

The method is conducted in the presence of an organic solvent which forms an azeotrope with water, thereby allowing water removal at lower temperatures than the temperatures used in conventional distillation methods. It is preferred that the organic solvent comprise about 10 to 40 weight percent of the weight of the mixture comprising solid potassium hydroxide and polyorganosiloxane and that the azeotrope have a boiling point within the range of about 90° C. to 120° C. Most preferred is when the organic solvent comprises about 20 to 30 weight percent of the weight of the mixture comprising solid potassium hydroxide and polyorganosiloxane.

Organic solvents useful in the present method are solvents which form an azeotrope with water and from which water can be separated. Examples of organic solvents useful in the present method are cyclohexane, toluene, xylene, diethyl ether, benzene, butanol, and methanol. The preferred organic solvent is cyclohexane at a concentration within the range of about 10 to 40 weight percent of the weight of the mixture comprising solid potassium hydroxide and polyorganosiloxane. The most preferred cyclohexane concentration is within the range of about 25 to 35 weight percent of the weight of the mixture comprising solid potassium hydroxide and polyorganosiloxane. The particular organic solvent and concentration can also be selected to control the temperature at which water is removed by azeotropic distillation and the rate at which water is removed.

The polyorganosiloxanes useful in the present method may be cyclic or linear, or may be a mixture of cyclic and linear polyorganosiloxanes. The cyclic polyorganosiloxanes have the formula $(R^2_2SiO)_n$, where n is an integer from 3 to about 20, $R^2$ is a hydrogen atom or an independently selected substituted or unsubstituted monovalent hydrocarbon group comprising from 1 to about 8 carbon atoms. $R^2$ can be for example, an alkyl group such as methyl, ethyl and propyl; a cycloalkyl group such as cyclohexyl and cyclopentyl; an alkenyl group such as vinyl and allyl; an aryl group such as phenyl and diphenyl; an alkaryl group such as tolyl and xylyl; an aralkyl group such as benzyl and phenylethyl; a halogenated alkyl group such as 3,3,3-trifluoropropyl and 4-chlorobutyl; and a halogenated aryl group such as chlorophenyl and dibromophenyl. Examples of cyclic polyorganosiloxanes useful in the present method are hexamethylcyclotrisiloxane, octamethylcyclotetrasiloxane, heptamethylcyclotetrasiloxane, hexaethylcyclotrisiloxane, and octaethylcyclotetrasiloxane. The preferred cyclic polyorganosiloxane for use in the present method is octamethylcyclotetrasiloxane.

The linear polyorganosiloxanes useful in the method are described by formula $R^1R^2_2SiO(R^2_2SiO)_mR^3$, where m $R^1, R^2$ and $R^3$ are as previously described. The linear polyorganosiloxanes can be for example, hexamethyldisiloxane, hexaethyldisiloxane, pentamethyldisiloxane and heptamethyltrisiloxane. The preferred linear polyorganosiloxane is hexamethyldisiloxane.

The mole ratio of solid potassium hydroxide to polyorganosiloxane can be about 4 to 1. Preferred is when the mole ratio of solid potassium hydroxide to polyorganosiloxane can be about 3 to 1. Most preferred is when the mole ratio of solid potassium hydroxide to polyorganosiloxane can be about 2 to 1.

The mixture comprising solid potassium hydroxide and a polyorganosiloxane in the presence of an organic solvent which forms an azeotrope with water, is heated to a temperature within a range of about 90° C. to 150° C. to facilitate reaction of the potassium hydroxide with the polyorganosiloxane thereby forming a potassium silanolate. Preferred is when the mixture in the presence of an organic solvent which forms an azeotrope with water is heated to a temperature within the range of about 110° C. to 130° C. Preferably the reaction is effected in an inert gas atmosphere, such as nitrogen, to prevent the mixture from absorbing moisture from the atmosphere which would later require removal from the mixture.

In the present method the method of recovering the potassium silanolate is not critical. For example, the potassium silanolate can be drained or poured from a reactor or kettle. In the preferred embodiment of the present method, water is removed from the potassium silanolate before it is recovered by azeotropic distillation. Water is removed from the potassium silanolate by an organic solvent which forms an azeotrope with water at a temperature within a range of about 90° C. to 150° C. In the method as water is removed from the mixture, the organic solvent is condensed and allowed to return to the mixture. The azeotropic distillation is continued until the water is removed. It is preferred that the azeotropic distillation be conducted within a temperature range of about 95° C. to 125° C. for about 4 hours to 5 hours. It is more preferred that the azeotropic distillation be conducted within a temperature range of about 100° C. to 120° C. Most preferred is when the azeotropic distillation is conducted within a temperature range of about 100° C. to 110° C.

In the present method stripping is not required, but it may be desirable to strip residual organic solvent and water contained in the organic solvent from the potassium silanolate. The stripping method is not critical, for example, the organic solvent may be stripped by distillation. The organic solvent is stripped from the potassium silanolate at a temperature within a range of about 80° C. to 150° C., at atmospheric pressure, under a nitrogen blanket. More preferred is when the organic solvent is stripped from the potassium silanolate at a temperature within a range of about 80° C. to 110° C. and at a pressure of about 100 mm Hg. Most preferred is when the organic solvent is stripped from the potassium silanolate at a temperature within a range of about 90° C. to 100° C. and at a pressure of about 40 mm Hg.

The following examples are provided to illustrate the present invention. These examples are not intended to limit the scope of the claims herein.

EXAMPLE 1

The ability to make a potassium silanolate having low branching using solid potassium hydroxide was evaluated. Octamethylcyclotetrasiloxane (200 g, 0.68 mole) was dissolved in cyclohexane (69 g) in a flask equipped with a mechanical stirrer, heating mantle, and a condenser. Solid potassium hydroxide pellets (9.9 g) were added to the flask under a nitrogen purge and moderate agitation. The mixture was heated to remove water by azeotropic distillation at a temperature of about 110° C. and distillation continued for 4 to 5 hours. At the end of azeotropic distillation the mixture temperature was 120° C. A total of 2.5 grams of water were removed from the flask by azeotropic distillation. Cyclohexane and water were stripped from the product by distilling at 150° C. for one hour at 40 mm Hg. The resulting product was a clear, viscous potassium silanolate. The potassium silanolate was analyzed using gas chromatography and determined to have a degree of branching of 800 ppm.

EXAMPLE 2

The ability to make potassium silanolate using aqueous potassium hydroxide was evaluated. Octamethylcyclotetrasiloxane (200 g, 0.68 mole) was dissolved in cyclohexane (69 g) in a flask equipped with a mechanical stirrer, heating mantle and a condenser at 90° C. Then an aqueous potassium hydroxide solution (22 g) consisting of 45 weight percent KOH in water (9.9 grams KOH, 0.18 mole) was added to the flask over a 0.5 hour period. The mixture was heated to remove water by azeotropic distillation at a temperature of about 95° C. and distillation continued for 12 hours. At the end of azeotropic distillation the temperature was 125° C. During the 12 hour distillation, a total of 12.6 grams of water were removed from the flask by azeotropic distillation. Recorded in Table 1 are the water removed in one hour increments and the percent water remove. Cyclohexane was stripped from the product by distilling at 150° C. for 9 hours at atmospheric pressure. The resulting product was a clear, viscous potassium silanolate. The potassium silanolate was analyzed using gas chromatography and determined to have a degree of branching of 9550 ppm. Within a few days the potassium silanolate became cloudy and separated into three distinct phases.

TABLE 1

| Water Removal At Elapsed Time (hours) | Water Removed (ml) | Percent Water Removed (%) |
|---|---|---|
| 1 | 2.5 | 18.2 |
| 2 | 4.8 | 34.7 |
| 3 | 5.8 | 42.0 |

TABLE 1-continued

| Water Removal At Elapsed Time (hours) | Water Removed (ml) | Percent Water Removed (%) |
|---|---|---|
| 4 | 6.5 | 47.4 |
| 5 | 7.0 | 51.1 |
| 6 | 7.4 | 54.1 |
| 8 | 12.0 | 87.6 |
| 9 | 12.5 | 91.2 |
| 10 | 12.5 | 91.2 |
| 11 | 12.5 | 91.2 |
| 12 | 12.6 | 91.7 |

We claim:

1. A method for the preparation of potassium silanolates comprising reacting a mixture comprising solid potassium hydroxide and a polyorganosiloxane described by formula $R^1R^2_2SiO(R^2_2SiO)_mR^3$ or $(R^2_2SiO)_n$, where m is an integer from 1 to about 1000, n is an integer from 3 to about 20, $R^1$ is a hydroxyl group or an alkoxy group comprising from 1 to about 8 carbon atoms and $R^2$ is a hydrogen atom or an independently selected substituted or unsubstituted monovalent hydrocarbon group comprising from 1 to about 8 carbon atoms, $R^3$ is a hydrogen atom or an alkyl group comprising from 1 to 8 carbon atoms in the presence of an organic solvent which forms an azeotrope with water at a temperature within a range of about 90° C. to 150° C. thereby forming a potassium silanolate.

2. A method according to claim 1, where the organic solvent comprises about 10 to 40 weight percent of the weight of the mixture and the azeotrope has a boiling point within a range of about 90° C. to 120° C.

3. A method according to claim 1, where the organic solvent comprises about 20 to 30 weight percent of the weight of the mixture.

4. A method according to claim 1, where the organic solvent is cyclohexane.

5. A method according to claim 4, where cyclohexane concentration is within the range of about 10 to 40 weight percent of the weight of the mixture.

6. A method according to claim 4, where the cyclohexane concentration is within the range of about 25 to 35 weight percent of the weight of the mixture.

7. A method according to claim 1, where the polyorganosiloxane is octamethylcyclotetrasiloxane.

8. A method according to claim 1, where the mole ratio of the solid potassium hydroxide to the polyorganosiloxane is about 4 to 1.

9. A method according to claim 1, where the mole ratio of the solid potassium hydroxide to the polyorganosiloxane is about 2 to 1.

10. A method according to claim 1, where the temperature is within a range of about 110° C. to 130° C.

11. A method according to claim 1, where the organic solvent forms an azeotrope with water at a temperature within a range of about 95° C. to 125° C.

12. A method according to claim 1, where the organic solvent forms an azeotrope with water at a temperature within a range of about 100° C. to 120° C.

13. A method according to claim 1, where the organic solvent forms an azeotrope with water at a temperature within a range of about 100° C. to 110° C.

14. A method according to claim 1, where the organic solvent is cyclohexane and the temperature is within a range of about 95° C. to 125° C.

15. A method according to claim 1, where the organic solvent is cyclohexane and the temperature is within a range of about 100° C. to 120° C.

16. A method according to claim 1, where the organic solvent is cyclohexane and the temperature is within a range of about 100° C. to 110° C.

17. A method according to claim 1, further comprising stripping the organic solvent from the potassium silanolate at a temperature within the range of about 80° C. to 150° C.

* * * * *